(12) United States Patent
Ranganathan

(10) Patent No.: US 11,331,515 B2
(45) Date of Patent: May 17, 2022

(54) METHOD OF OPTIMIZING COLLIMATOR TRAJECTORY IN VOLUMETRIC MODULATED ARC THERAPY

(71) Applicant: KONINKLIJKE PHILIPS N.V., Eindhoven (NL)

(72) Inventor: Vaitheeswaran Ranganathan, Bangalore (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 403 days.

(21) Appl. No.: 16/344,854

(22) PCT Filed: Oct. 30, 2017

(86) PCT No.: PCT/EP2017/077830
§ 371 (c)(1),
(2) Date: Apr. 25, 2019

(87) PCT Pub. No.: WO2018/083072
PCT Pub. Date: May 11, 2018

(65) Prior Publication Data
US 2020/0054895 A1 Feb. 20, 2020

Related U.S. Application Data

(60) Provisional application No. 62/418,305, filed on Nov. 7, 2016.

(51) Int. Cl.
*A61N 5/10* (2006.01)
*G16H 20/40* (2018.01)
(52) U.S. Cl.
CPC ......... *A61N 5/1031* (2013.01); *A61N 5/1047* (2013.01); *A61N 5/1081* (2013.01); *G16H 20/40* (2018.01)

(58) Field of Classification Search
CPC .. A61N 5/1031; A61N 5/1047; A61N 5/1081; A61N 5/103; G16H 20/40
See application file for complete search history.

(56) References Cited

U.S. PATENT DOCUMENTS

2004/0190680 A1  9/2004 Chang
2005/0054409 A1  3/2005 Cannon
(Continued)

OTHER PUBLICATIONS

Yu et al.: "Intensity-Modulated Arc Therapy With Dynamic Multileaf Collimation: An Alternative to Tomotherapy", Physics in Medicine and Biology, Institute of Physics Publishing, Bristol GB, vol. 40, Jan. 1, 1995.

(Continued)

*Primary Examiner* — Kaylee R Wilson

(57) ABSTRACT

In a continuous arc radiation therapy planning method for planning a radiation therapy session parameterized by a set parameters for control points (CPs) along at least one radiation source arc, a geometric optimization (40) is performed that does not include calculating radiation absorption profiles to generate optimized values for a sub-set of the parameters. After the geometric optimization, a main optimization (42) is performed that includes calculating radiation absorption profiles. The main optimization is performed with the sub-set of parameters initialized to the optimized values from the geometric optimization. The sub-set of parameters optimized by the geometric optimization may include collimator angle parameters for a multileaf collimator (MLC) (58). The geometric optimization may optimize a cost function comprising a sum over the CPs of a per-CP cost function dependent on a target-only region (62) defined as a planning target volume excluding any portion overlapping an organ at risk.

23 Claims, 5 Drawing Sheets

(56) References Cited

U.S. PATENT DOCUMENTS

2006/0256915 A1    11/2006  Otto
2008/0285719 A1    11/2008  Nord
2013/0142310 A1     6/2013  Fahimian

OTHER PUBLICATIONS

International Search Report and Written Opinion dated Feb. 22, 2018 for International Application No. PCT/EP2017/077830 Filed Oct. 30, 2017.
Zhang et al: "Optimization of collimator trajectory in volumetric modulated arc therapy: development and evaluation for paraspinal SBRT." International Journal of Radiation Oncology* Biology* Physics 77.2 (2010): 591-599.

METHOD OF OPTIMIZING COLLIMATOR TRAJECTORY IN VOLUMETRIC MODULATED ARC THERAPY

CROSS REFERENCE TO RELATED APPLICATIONS

This application is the U.S. National Phase application under 35 U.S.C. § 371 of International Application No. PCT/EP2017/077830 filed Oct. 30, 2017, published as WO 2018/083072 on May 11, 2018, which claims the benefit of U.S. Provisional Patent Application No. 62/418,305 filed Nov. 7, 2016. These applications are hereby incorporated by reference herein.

FIELD

The following relates generally to the radiation therapy arts, inverse modulated radiation therapy planning arts, modulated arc radiation therapy arts, and the like.

BACKGROUND

Volumetric Modulated Arc Therapy (VMAT) delivers radiation during rotation of the gantry of a linear accelerator (linac) through one or more arcs with the radiation continuously on. As it does so, a number of parameters may be varied, such as the aperture shape defined by a multi-leaf collimator (MLC), the collimator angle of the MLC, the fluence-output rate ("dose rate"), the gantry rotation speed, and the translational position and/or rotational orientation of the patient support couch. In planning a VMAT session, the continuous arc is discretized into a set of control points (CPs) along the continuous arc, and parameters at each CP are optimized. The success of VMAT depends on how the various variables are optimized per CP. As compared to static intensity-modulated radiation therapy (IMRT) delivery, VMAT delivery is fast and efficient.

In VMAT, as in any type of intensity modulated radiation therapy, there is a trade-off between delivering radiation to the planning target volume (PTV), which is usually a malignant tumor or the like, and avoiding irradiation of neighboring organs at risk (OARs). In practice, it is usually impossible to avoid some radiation exposure to OARs, and so the oncologist or other medical professional specifies dose objectives, such as a target and/or minimum radiation dose objective to be delivered to the PTV and maximum permissible dose objectives for each OAR (which may in general be different for different OARs). The dose objectives may be specified as hard limits, soft constraints, or some combination thereof. To ensure the entire PTV is irradiated, the beam's eye view (BEV) should encompass the entire PTV for at least a portion of the arc. The planning includes designing collimator leaf settings for each CP that block radiation from reaching OARs, while still achieving the dose objectives for radiation delivery to the PTV.

The number of parameters that can be optimized during planning of a VMAT session is large. At each CP the following are a typical set of parameters that are available for adjustment: a setting for each collimator leaf of the MLC; the collimator angle; instantaneous gantry rotation speed; three couch translational degrees of freedom; and three couch rotational degrees of freedom. The total number of parameters available for adjustment is the number of such parameters at each CP multiplied by the number of CPs. To provide reasonably accurate discretization of the arc, the number of CPs should be relatively large.

The continuous movement of the linac over the arc through the successive CPs also imposes certain constraints on certain parameters. For example, the maximum ramp rate for changing gantry rotation speed imposes limits on the maximum change in instantaneous gantry rotation speed between successive CPs. Similarly, there is a maximum speed at which the collimator angle can be changed. Some constraints may be interrelated—for example, all else being equal a faster gantry rotation speed will reduce the time interval between passage of the beam source through two successive CPs, which in turn reduces the maximum collimator angle change that can be achieved between the two successive CPs.

To improve computational efficiency, this large parameter space is usually reduced by setting certain parameters, such as the collimator angle, to a fixed value (e.g. 0 degrees) for all CPs. Gantry speed and/or fluence output rate may also be set to a constant values. Improved performance can be obtained by setting the values of certain such fixed parameters on the basis of some physical rationale. For example, if the most critical organ at risk (OAR) is the spine it may be beneficial to set the collimator angle for each CP so that the long dimension of the collimator leaves is roughly parallel with the spine, so as to roughly align the collimator leaves with the spinal OAR.

In general, there is a balance between reducing planning computational complexity and achieving highest fidelity of the resulting VMAT plan with the dose objectives. Setting more parameters constant reduces computational complexity but will likely reduce fidelity of the optimized plan to the dose objectives. This trade-off means that sub-optimal fidelity to the dose objectives is accepted in return for improved computational speed by way of fixing some parameter values.

The following discloses new and improved systems, device, and methods.

SUMMARY

In one disclosed aspect, a non-transitory storage medium stores instructions readable and executable by a computer to perform a continuous arc radiation therapy planning method for planning a radiation therapy session parameterized by a set of parameters for control points (CPs) along at least one radiation source arc. The planning method comprises performing a geometric optimization that does not include calculating radiation absorption profiles to generate optimized values for a sub-set of the set of parameters. After completion of the geometric optimization, a main optimization is performed that includes calculating radiation absorption profiles. The main optimization is performed with the sub-set of the set of parameters initialized to the optimized values for the sub-set generated by the geometric optimization. A radiation therapy plan comprising optimized values for the set of parameters output by the main optimization is stored in a non-transitory radiation therapy plans storage.

In another disclosed aspect, a radiation therapy planning device is disclosed. A computer is programmed to perform a continuous arc radiation therapy planning method for planning a radiation therapy session parameterized by a set of parameters for control points (CPs) along at least one radiation source arc. The planning method comprises (i) performing a geometric optimization to generate optimized values for a sub-set of the set of parameters including at least collimator angle parameters specifying collimator angles of a multileaf collimator at the CPs along the at least one radiation source arc and (ii) after completion of the geometric optimization, performing a main optimization with the sub-set of the set of parameters initialized to the optimized values for the sub-set generated by the geometric optimization. A non-transitory storage medium is operatively connected with the computer to store a radiation therapy plan comprising optimized values for the set of parameters output by the main optimization.

In another disclosed aspect, a method includes planning a continuous arc radiation therapy session parameterized by a set of parameters for control points (CPs) along at least one radiation source arc. An initial optimization is performed, including adjusting values for a sub-set of the set of parameters to optimize a cost function comprising a sum over the CPs along the at least one radiation source arc of a two dimensional (2D) per CP cost function wherein the per-CP cost function depends on one or more 2D regions in the beam's eye view (BEV) of the CP. After completing the initial optimization, a main optimization is performed with the sub-set of the set of parameters initialized to the values for the sub-set generated by the initial optimization. A radiation therapy plan is generated comprising optimized values for the set of parameters output by the main optimization. The initial optimization, the main optimization, and the generating of the radiation plan are suitably performed by a computer.

One advantage resides in providing improved fidelity of a continuous arc radiation therapy session plan to dose objectives.

Another advantage resides in providing more computationally efficient continuous arc radiation therapy session planning.

Another advantage resides in providing improved fidelity of a continuous arc radiation therapy session plan to dose objectives in combination with more computationally efficient continuous arc radiation therapy session planning.

Another advantage resides in employing a reduced number of fixed parameters during continuous arc radiation therapy session planning without (or with reduced) concomitant increase in computational complexity.

Another advantage resides in providing an improved metric for optimizing collimator angle during continuous arc radiation therapy session planning.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention. Unless otherwise noted, the drawings are diagrammatic and are not to be construed as being to scale or to illustrate relative dimensions of different components.

DETAILED DESCRIPTION

In embodiments disclosed herein, an improved planning sequence is disclosed for continuous arc radiation therapy planning, in which the conventional plan optimization is divided into two independent optimization steps: a geometric optimization which optimizes certain chosen parameters of the continuous arc radiation therapy with respect to a chosen cost function that depends on geometric inputs, and a main optimization which optimizes the continuous arc radiation therapy parameters with the parameters that were optimized in the geometric optimization held to the values determined in the geometric optimization. Alternatively, in the main optimization the parameters that were optimized in the geometric optimization may be set to the values determined in the geometric optimization as initial values but allowed to be adjusted by the main optimization. The geometric optimization is chosen to be computationally efficient, for example formulated as a geometric optimization with PTV and OAR contours as inputs. The geometric optimization does not entail computing radiation absorption profiles using a radiation attenuation map of the patient, and in some embodiments is formulated as a two-dimensional (2D) geometric optimization which does not require computing three-dimensional (3D) volume rotations. The geometric optimization is therefore fast since it avoids computationally complex radiation absorption profile computations, and optionally also avoids 3D volume rotation calculations.

In the illustrative embodiments, the parameters that are optimized during the geometric optimization include the collimator angle at each CP, and optionally may also include the gantry rotation speed at each CP. The gantry rotation speed and collimator rotation speed (i.e. the speed at which the MLC rotates) impose a limit on the maximum change in collimator angle achievable between successive CPs; hence optimizing collimator angle and gantry rotation speed, and optionally also the collimator rotation speed, together in the geometric optimization is a synergistic process. Optimization of these parameters can advantageously be formulated as a 2D geometric optimization that does not require computing radiation absorption profiles. In some embodiments, a cost function employed in a 2D geometric optimization is defined in terms of a "target-only region". The target-only region is the area of the PTV as seen from the BEV at the CP excluding any portion(s) of the PTV overlapping an OAR.

Figure 1:
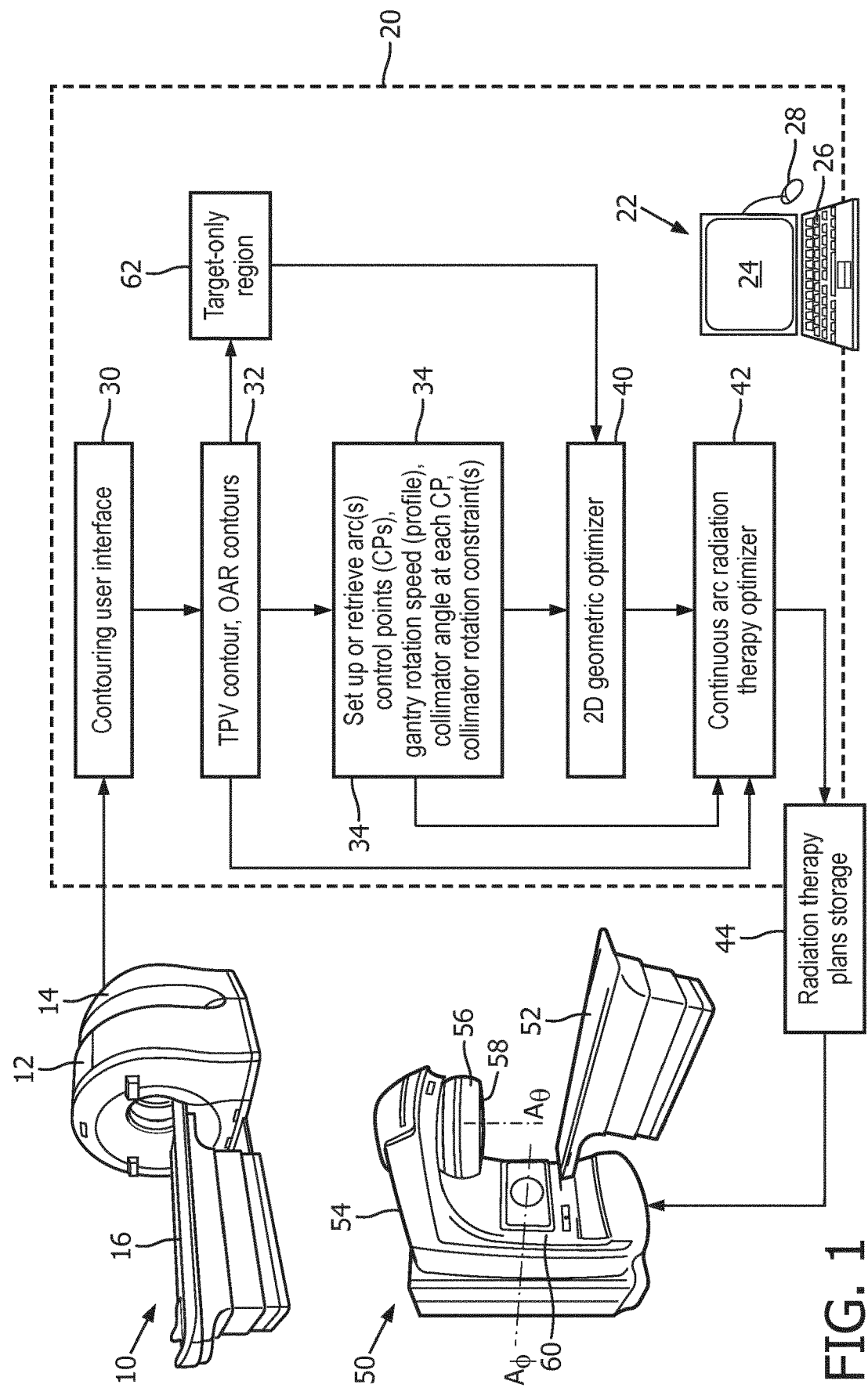
FIG. 1 diagrammatically shows a system for planning and executing a continuous arc radiation therapy session.

With reference to FIG. 1, a continuous arc radiation therapy planning and delivery system is diagrammatically shown. The radiation therapy may be any type of continuous arc radiation therapy, such as Volumetric Modulated Arc Therapy (VMAT), Intensity Modulated Arc Therapy (IMAT), or so forth. The number of arcs executed in the therapy session may, in general, be one, two, three, or more. To initiate the session, planning images are first acquires of the patient or other subject using an illustrative multi-modal imaging device 10 that includes an illustrative computed tomography (CT) imaging gantry 12 and an illustrative positron emission tomography (PET) imaging gantry 14 with a common patient couch 16 for moving the patient into one and/or the other imaging gantries 12, 14. The imaging device 10 may, by way of non-limiting illustration, be an Ingenuity™ time-of-flight (TF) PET/CT scanner, a Gemini™ TF PET/CT scanner, or a TruFlight™ TF PET/CT scanner (each available from Koninklijke Philips N.V., Eindhoven, the Netherlands). Additional or other imaging modalities may be employed for acquiring the planning images, such as magnetic resonance (MR) images acquired using an MR imaging device, single photon emission computed tomography (SPECT) images acquired using a gamma camera, and/or so forth. The planning images are processed by a continuous arc radiation therapy planning device 20 comprising a computer 22 (e.g. a desktop computer, network server computer, various combinations thereof, or so forth) that is programmed to provide a user interface and computational processing to generate a radiation therapy plan using planning images acquired by the imaging device 10. For facilitating user interfacing, the computer 22 includes or has access to at least one display 24 (e.g. an LCD display, plasma display, or so forth) and one or more user input devices such as an illustrative keyboard 26, mouse 28, a touch-sensitive overlay of the display 24, and/or so forth.

The computer 22 is programmed to provide a contouring graphical user interface (contouring GUI) 30 via which an oncologist, radiologist, or other medical professional can draw 2D and/or 3D contours delineating a planning target volume (PTV) to be irradiated by the continuous arc radiation therapy and one or more organ at risk (OAR) contours delineating one or more OARs whose permissible radiation exposure is to be controlled or limited. The contouring GUI 30 can operate in various known ways. For example, the user may manually draw 2D contours around the PTV or OAR in various 2D slices of a 3D planning image using a pointing device such as the mouse 28 or a touch screen, and the computer 22 is programmed to interpolate between these 2D contours to generate a 3D contour (sometimes called a mesh) delineating the PTV or OAR. In a more automated approach, the user may identify a small number of landmarks that mark boundary points of the PTV or OAR and the computer 22 is programmed to define an initial 3D mesh including these landmarks and then fit the initial mesh to the PTV or OAR using a mesh fitting approach that detects feature edges based on spatial gradients or the like. In a fully automated approach the initial mesh may be automatically generated based on a reference geometry, and the fitted mesh presented to the user for final adjustment (if needed) and approval. These are merely illustrative examples, and other approaches for delineating a set of contours 32 may be employed. Typically, the set of contours 32 includes a contour delineating the PTV and one or more contours delineating neighboring OARs.

In an operation 34, the continuous arc radiation therapy session is configured. This includes setting up or retrieving (e.g., from a database of continuous arc radiation therapy session configuration files) the one or more arcs the radiation source is to traverse, and setting up or retrieving the control points (CPs) along each such arc. Initial gantry rotation speed (if constant) or speed profile (if varying along the arc) is set up or retrieved. The gantry rotation speed (profile) may be fixed or may be optimized during the subsequent optimizations. Similarly, an initial collimator angle for the MLC is set up or retrieved for each CP. These are initial values as the collimator angle at each CP is a parameter to be optimized. In some cases, the collimator angle at each CP may be initialized to a default value such as 0°. The operation 34 further includes setting up or retrieving one or more constraints on the collimator rotation. The constraint(s) may be formulated in various ways. In one approach, a maximum collimator rotation speed is set, and the constraints are then determined as a maximum collimator angle change between each two successive CPs along the arc which can be computed as the maximum collimator rotation speed multiplied by time interval between traversal of the successive CPs. (As illustration, if the maximum collimator rotation speed is 5°/sec and the gantry rotation speed causes the radiation source to pass from one CP to the next CP in a time interval of 2 sec, then the maximum collimator angle change between these two CPs is 5°/sec×2 sec=10°). This approach requires knowledge of the gantry rotation speed (profile)—in a simpler approach, a maximum collimator angle change between successive CPs is chosen to be low enough to be physically realizable for any gantry rotation speed that may be credibly used during the continuous arc radiation therapy. Other configuration aspects may be set up or retrieved, such as fluence-output rate ("dose rate") and the translational position and/or rotational orientation of the patient support couch. Again, these may be initial values that are later optimized, or may be fixed values. The configuration of the radiation therapy session may also include set up or retrieval of information pertaining to the type of radiation (e.g. x-rays, gamma rays, electron beam, et cetera), the radiation particle energy (e.g. x-ray wavelength or photon energy), radiation beam angle, radiation source-to-patient distance, and/or so forth.

After set up and/or retrieval of the continuous arc radiation therapy configuration, an optimizer is applied to optimize various adjustable parameters of the continuous arc radiation therapy. In general, the configured continuous arc radiation therapy session is parameterized by a set of parameters for the CPs along the at least one radiation source arc. By way of non-limiting illustration, the set of parameters may include: settings for the leaves of the MLC at each CP; collimator angle at each CP; collimator rotation speed; dose rate at each CP; and instantaneous gantry rotation speed at each CP; and couch translational and/or rotational positions. Conventionally, all these parameters are optimized in an iterative optimization using a cost function that measures fidelity of a calculated dose distribution in the patient with dose objectives assigned by the oncologist or other medical professional. The dose distribution is calculated for the current-iteration parameter values using a radiation absorption map for the patient, e.g. computing for each CP the radiation absorption profile in the patient along paths extending from the radiation source into the patient and then summing these radiation absorption profiles to compute the total dose delivered to each "voxel" of the patient. The dose distribution may be integrated over the PTV and over each OAR to determine a total dose to the PTV and each OAR. A peak dose in each of the PTV and each OAR may be determined as the voxel belonging to each such region having highest total dose summed over all CPs. Other dose metrics might be computed depending upon the particular formulation of the dose objectives provided by the medical professional. Based on the comparison of these computations and the dose objectives, various parameters are adjusted, e.g. by taking partial derivatives respective to the various parameters under adjustment (e.g. a Jacobean) and employing an optimization algorithm such as a gradient descent method, Levenberg-Marquardt, or the like to adjust parameter values to reduce the difference between the calculated values and the prescribed dose objectives. This process is repeated iteratively to adjust the parameter values iteratively until the calculated values converge to an acceptable fidelity with the prescribed dose objectives.

It will be appreciated that the foregoing optimization is computationally complex and ties up substantial computing resources of the computer 22 and also takes a substantial amount of time. To reduce computational complexity of the optimization and increase speed of the planning process, it is known to set some parameters to fixed values. By effectively removing these fixed parameters from the optimization process, computational complexity is reduced and processing speed is enhanced. However, this is achieved at a substantial cost in that the fixed parameter values may not be optimal for the patient, and the fidelity of the calculated dose distribution for the resulting radiation therapy plan to the dose objectives may be reduced as a consequence.

With continuing reference to FIG. 1, in approaches disclosed herein an improved optimization sequence employs an initial geometric optimization 40 followed by a more conventional VMAT optimization 42 (or other continuous arc radiation therapy optimization, e.g. an IMAT optimization). The geometric optimization 40 optimizes a sub-set of the set of parameters of the continuous arc radiation therapy with respect to a cost function that can be efficiently computed, for example depending on geometric inputs but not requiring computation of radiation absorption profiles using an absorption map. For example, the cost function can be a geometric cost function having as inputs the PTV and OAR contours. The geometric optimization 40 is in some embodiments performed on a per-CP basis as a 2D geometric optimization which does not require computing 3D volume rotations. The geometric optimization 40 is therefore fast since it avoids computationally complex radiation absorption profile computations, and optionally also avoids 3D volume rotation calculations. As such, the choice of the sub-set of parameters optimized by the geometric optimization 40 is chosen to be effectively optimized under these limitations. For example, optimizing the dose rate is generally done by taking into account the radiation absorption profiles, and hence dose rate is not easily optimized during the geometric optimization 40. Similar issues arise when optimizing MLC leaves, since they are typically chosen to precisely tailor the 3D dose distribution which generally calls for computing the radiation dose profiles in the patient. Likewise, optimizing couch rotational parameters entails performing 3D volume rotations, and accordingly is not well-suited for the geometric optimization 40. On the other hand, optimizing the couch translational parameters may optionally be done during the geometric optimization 40.

In the illustrative embodiments, the geometric optimization 40 is used to optimize the collimator angle parameters, and optionally also the gantry rotation speed parameter (if fixed over the arc) or parameters (if speed is variable over the arc). In general, the optimal collimator angle is controlled principally by region-level orientation of the PTV and OAR regions, which can be determined by purely geometrical considerations. However, the collimator angle is also constrained by the physically realizable rate at which the collimator angle can be adjusted. In view of this, the gantry rotation speed parameter(s) may usefully be optimized concurrently with the collimator angle parameters during the geometric optimization 40.

The geometric optimization 40 generates optimized values for a sub-set of the set of parameters that are optimized in the geometric optimization 40—in the illustrative examples, these parameters are the collimator angle parameter for each CP and optionally also the gantry rotation speed parameter(s). After completion of the geometric optimization 40, the main optimization 42 is performed, with the optimized values for the sub-set of parameters serving as initial values for that sub-set in the main optimization 42. The main optimization 42 may employ any type of optimization commonly used in planning a continuous arc radiation therapy session. For example, the main optimization 42 may calculate current-iteration parameter values using the radiation absorption map for the patient (which is preferably generated specifically for the patient, e.g. using the CT planning images, although use of a standard atlas absorption map is also contemplated, optionally with warping to the patient-specific anatomy as indicated in the planning images). The dose distribution is integrated over the PTV and over each OAR to determine a total dose to each region, and/or the peak dose for each region is calculated, or so forth, and a cost function is used to assess fidelity of the calculated total dose parameters with the dose objectives prescribed by the oncologist or other medical professional. Various parameters are then adjusted based on partial derivatives respective to the various parameters (e.g. a Jacobean) using gradient descent, Levenberg-Marquardt, or another optimization algorithm, and the process is repeated iteratively until the calculated values converge to an acceptable fidelity with the prescribed dose objectives. Again, this is merely an illustrative example and more generally any optimization algorithm suitable for continuous arc radiation therapy planning may be used in the main optimization 42.

The optimized values for the sub-set of parameters output by the geometric optimization 40 serve as initial values in the main optimization 42. That is, in the initial iteration of the main optimization 42 the sub-set is assigned the parameter values output by the geometric optimization 40. In some embodiments, the main optimization 42 is performed with the sub-set of the set of parameters held constant at the optimized values for the sub-set generated by the geometric optimization 40. In this case, the set of parameters output by the main optimization 42 includes the optimized values for the sub-set generated by the geometric optimization 40. This approach is computationally efficient as the sub-set of parameters is removed entirely from the main optimization 42. However, because the geometric optimization 40 uses a "surrogate" cost function rather than directly assessing fidelity to the dose objectives, these optimized values for the sub-set output by the geometric optimization 40 may be less optimal than could be produced if those parameters were adjusted by the main optimization 42.

Accordingly, in other embodiments the main optimization 42 includes adjusting values of the sub-set of the set of parameters. In these embodiments the optimized values for the sub-set generated by the geometric optimization 40 serve only as initial parameters which are further adjusted by the main optimization 42. In this case the parameters output by the main optimization 42 includes the optimized values for the sub-set generated by the geometric optimization 40 with the additional adjustment by the main optimization. In these embodiments, the execution speed of the main optimization 42 is improved by providing initial values for the sub-set of parameters that are expected to be close to the final optimized values after adjustment by the main optimization 42. Moreover, the resulting radiation therapy plan is expected to be more accurate because the main optimization 42 is started with "close" initial values for the sub-set of parameters. This is especially valuable in the case of the sub-set including the collimator angle because the impact of the values of the MLC leaf position parameters depends strongly on the collimator angle—thus, providing close initial values for the collimator angle at each CP facilitates achieving rapid convergence for the MLC leaf position parameters.

With continuing reference to FIG. 1, the computer 22 stores a radiation therapy plan comprising optimized values for the set of parameters output by the main optimization 42 in a non-transitory radiation therapy plans storage 44 which may be integral with the computer 22 (e.g. a hard drive of the computer) or accessible by the computer 22 (e.g. a network drive connected to the computer via a hospital data network, the Internet, or some combination thereof). More generally, the non-transitory radiation therapy plans storage 44 may be hard disk or other magnetic storage medium, and optical disk or other optical storage medium, a solid-state drive (SSD) or other electronic storage medium, various combinations thereof, or so forth. At the appointment time for the radiation therapy session, the patient is provided with continuous arc radiation therapy by a radiation therapy delivery apparatus 50, such as an illustrative linear accelerator (linac) 50. The patient is loaded onto a couch 52 of the linac 50. In some embodiments, the couch 52 provides three degrees of translational freedom of movement and optionally also three degrees of rotational freedom of movement, with couch position parameters of the optimized radiation therapy plan setting the could translational and rotational position for each CP. The illustrative linac 50 includes a linear electron beam accelerator 54 housed in a horizontal beam of the linac 50, which energizes an x-ray or gamma ray generator and associated hardware which serves as the radiation source 56. A multi-leaf collimator (MLC) 58 comprises adjustable leaves that can be set to shape the radiation beam at each CP. The MLC 58 can be rotated to a chosen collimator angle designated θ about a collimator axis designated as $A_θ$ in FIG. 1. The collimator angle parameters of the optimized radiation therapy plan specify the collimator angle θ at each CP. The continuous arc of motion of the radiation source 56 is provided by rotation of the radiation source gantry (including a main gantry body 60 and the horizontal beam containing the electron accelerator 54) about a gantry rotation axis designated as $A_φ$ in FIG. 1. A computer or other controller is programmed to operate the radiation therapy delivery apparatus 50 to deliver continuous arc radiation therapy to the patient in accordance with the radiation therapy plan stored in the plans storage 44. The computer or other controller operating the radiation therapy delivery apparatus 50 may be the same computer 22 that implements the continuous arc radiation therapy planning device 20, or (more typically) may be a different computer.

In the following, an illustrative example of operation of the continuous arc radiation therapy planning device 20 is described. In this example, the 2D geometric optimizer 40 employs a cost function comprising a sum over the CPs along the at least one radiation source arc of a 2D per-CP cost function which depends on one or more 2D regions in the beam's eye view (BEV) of the CP. In the specific illustrative example, the per-CP cost function depends on a target-only region 62 defined as the PTV excluding any portion of the PTV overlapping an OAR region. The PTV has a radiation dose objective and each OAR region has a maximum permissible radiation dose objective or constraint. The illustrative example also employs VMAT as the continuous arc radiation therapy.

Figure 2:
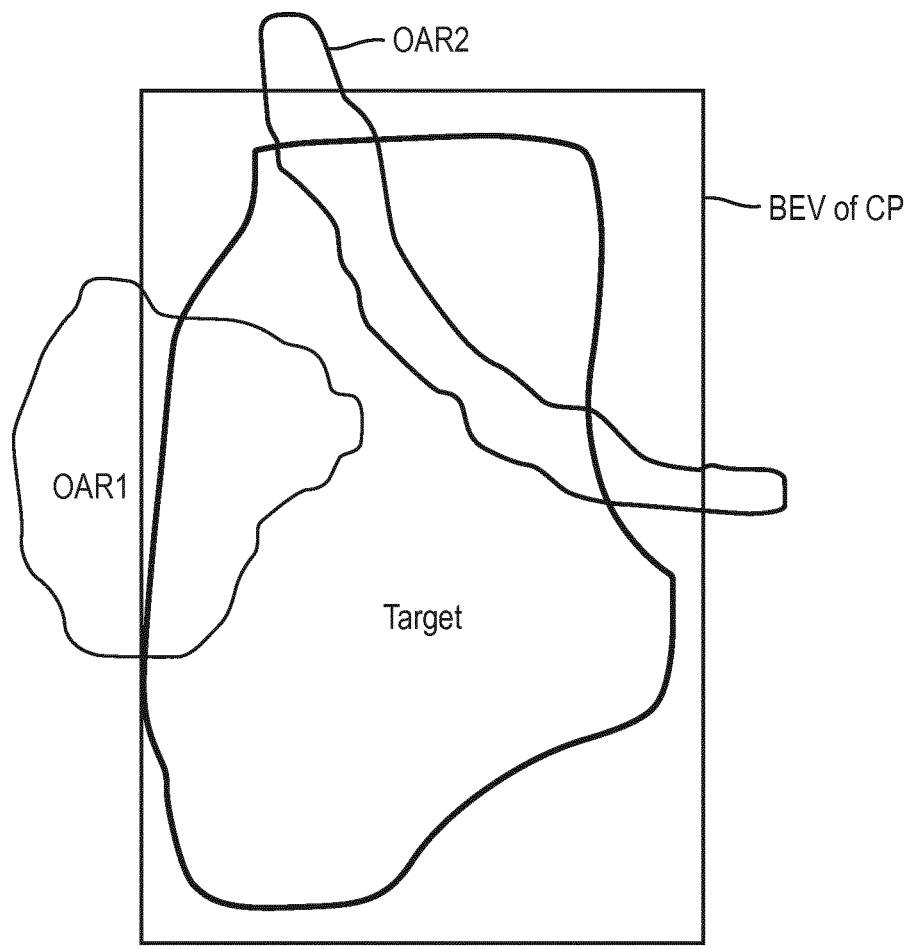
FIG. 2 diagrammatically shows a possible arrangement at a control point (CP) of a planning target volume (PTV, labeled "Target" in FIG. 2) and two organs at risk (OAR1 and OAR2), with a beam's eye view (BEV) superimposed.

With reference now to FIG. 2, before commencing VMAT optimization, control points CPs are placed at all gantry angles e.g. 0 to 360 deg at a user-specified minimum gantry angle spacing (e.g. 2 to 4 degrees spacing in some embodiments) with their BEVs initialized to cover full composite target volume (i.e. geometric sum of all PTVs). In FIG. 2, an illustrative example of the BEV for a single CP is shown. The PTV labeled as "Target" in FIG. 2) overlaps a first OAR region ("OAR 1") and a second OAR region ("OAR 2").

Figure 3:
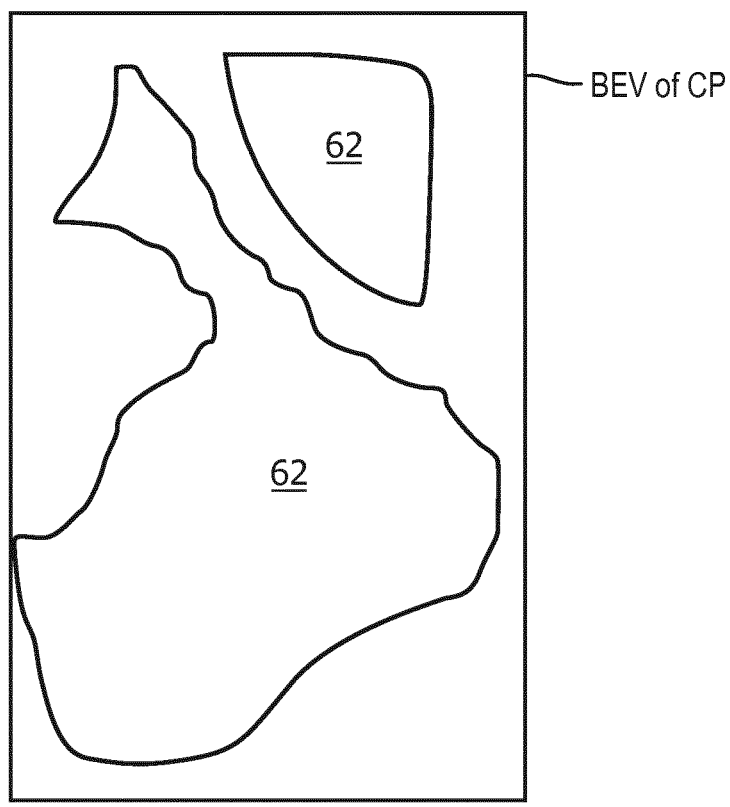
FIG. 3 diagrammatically shows the target-only region for the CP depicted in FIG. 2.

With reference to FIG. 3, the target-only region 62 is defined as the PTV excluding any portion of the PTV overlapping an OAR region. In the illustrative example of FIGS. 2 and 3, the target-only region 62 shown in FIG. 3 is obtained by taking the target region of FIG. 2 and removing any portion of the target region that is overlapped by either OAR 1 or OAR 2 (or both, though this does not occur in the illustrative example). It may be noted that the overlap occurs in the 2D BEV, and does not necessarily mean that the three-dimensional regions actually overlap. For example, the BEV of FIG. 2 can occur if OAR 1 (or OAR 2) is between the radiation source and the target volume, or if the target volume is between the radiation source and OAR 1 (or OAR 2). Thus, the dimensions of the PTV and OAR regions, and their overlap (if any) will in general be different for the BEV of different CPs along the arc.

In the illustrative geometric optimization, the goal is to expose the entire target-only region 62 while using leaves of the MLC 58 to completely block radiation exposure of all OARs (namely of both OAR 1 and OAR 2 in the example of FIGS. 2 and 3). In practice, this usually cannot be achieved for an arbitrary collimator angle, because some leaves may need to be inserted over a portion of the target-only region in order to ensure adequate blockage of radiation exposure to an OAR.

Figure 4:
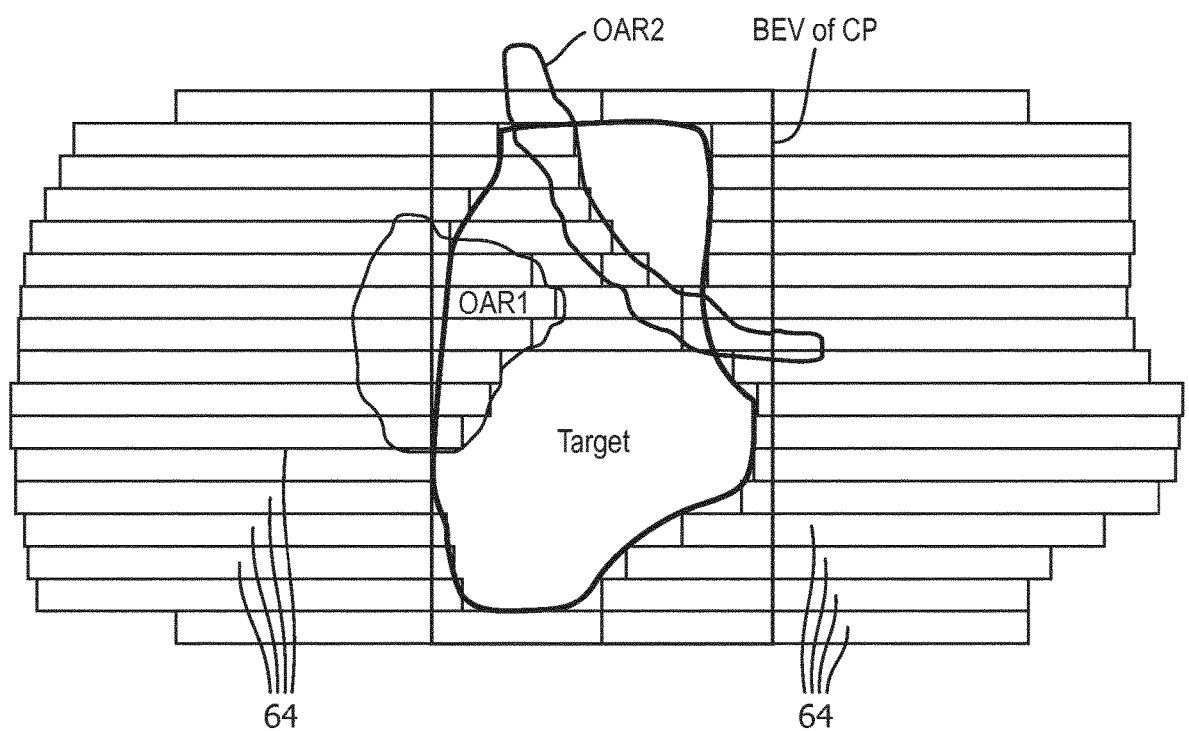
FIG. 4 diagrammatically shows the multileaf collimator (MLC) with collimator angle of zero degrees with the MLC leaf positions superimposed showing the leaf positions maximizing the portion of the target-only region that is exposed while completely shielding the OARs.
Figure 5:
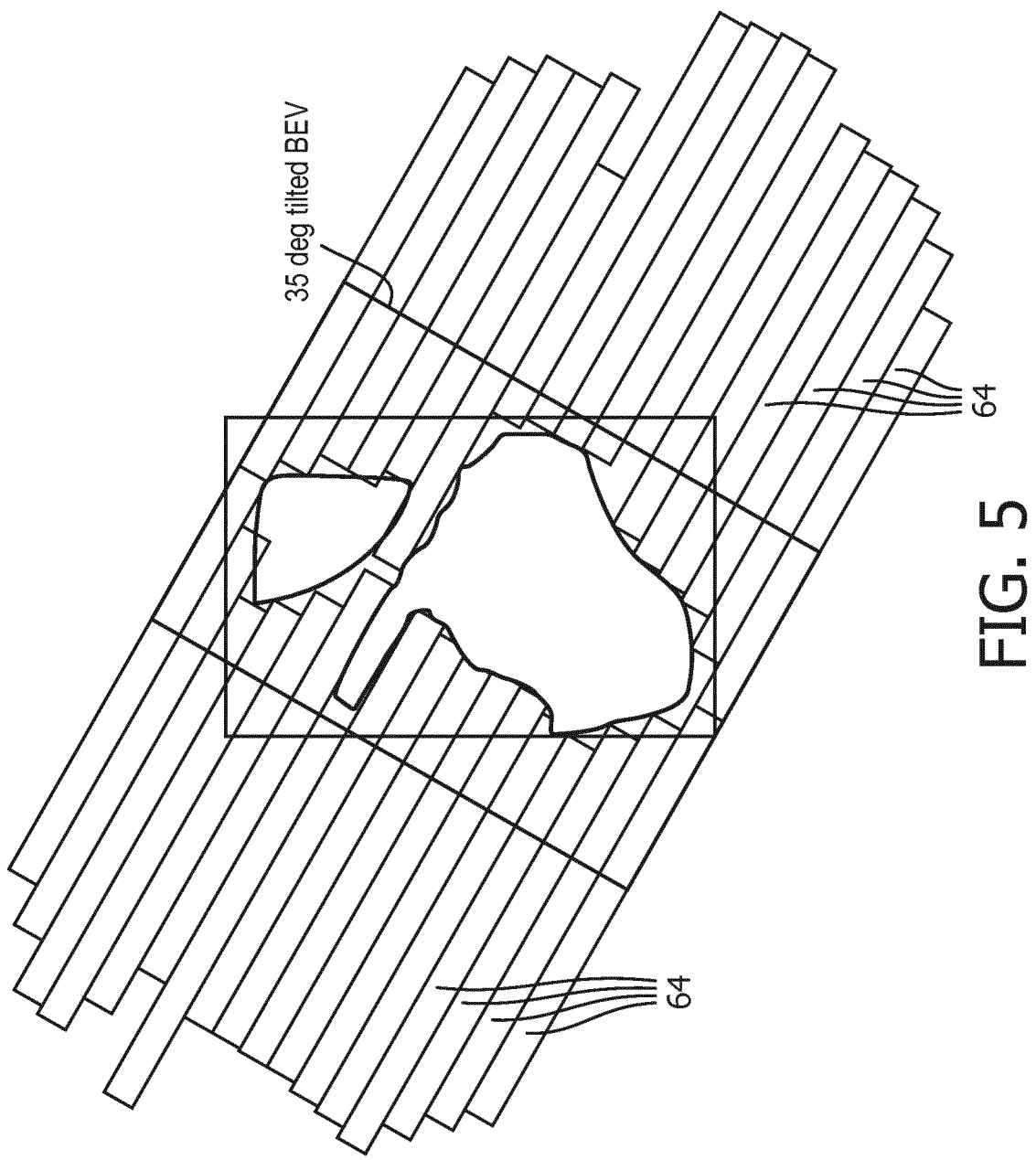
FIG. 5 diagrammatically shows the multileaf collimator (MLC) as in FIG. 4 but with the collimator angle optimized to maximize the portion of the target-only volume that is exposed while completely shielding the OARs.

With reference to FIGS. 4 and 5, at each CP a geometric optimization is performed by iteratively rotating the collimator angle θ such that at the resulting collimator angle θ the leaves 64 of the MLC can be arranged to expose the maximum portion of the target-only region 62 while completely shielding all OARs from radiation exposure. In order to perform this geometric optimization per CP, the following per-CP geometric cost function $F_{CP_i}(θ)$ is suitably employed for the ith control point (that is, for control point $CP_i$):

$$F_{CP_i}(θ)=(A_{CP_i}-A'_{CP_i}(θ))^2 \qquad (1)$$

In Equation (1), θ is the collimator angle to be optimized, $A_{CP_i}$ is the area of the entire target-only region 62 for control point $CP_i$ shown in FIG. 3, while $A'_{CP_i}(θ)$ is the maximum portion of the area $A_{CP_i}$ that is exposed for collimator angle θ with the leaves 64 of the MLC 58 set to completely block radiation exposure of all OARs. FIG. 4 shows the situation for collimator angle θ=0°. In this case, it will be noted that in order to completely shield OAR 2 it is necessary for the leaves on the upper left side (in the orientation of FIG. 4) to extend over a significant portion of the target-only area, so that the area $A'_{CP_i}(θ=0°)$ is significantly smaller than the area $A_{CP_i}$ of the target-only region 62. By contrast, as shown in FIG. 5, by tilting the collimator angle to a value θ=35° the area $A'_{CP_i}(θ=35°)$ is much closer to the area $A_{CP_i}$ of the target-only region 62. Intuitively, this is achieved because at θ=35° the leaves 64 of the MLC 58 are aligned with the elongated OAR 2 which overlaps the target volume.

The optimization of Equation (1) is for a single CP. However, Equation (1) cannot simply be optimized independently for each CP, because there is a constraint insofar as it is not possible to make arbitrarily large changes in the collimator angle θ between successive CPs. This is due to the finite maximum rate of change in the collimator angle and the finite time interval between traversal of the radiation source 56 from one CP to the next CP along the arc. Taking this into account, the geometric optimization 40 can be written as minimization of a cost function comprising sum over the CPs along the at least one radiation source arc of the 2D per-CP cost function of Equation (1):

$$\min_{\theta_i} \sum_{i=1}^{N} (A_i - A'_i(\theta_i))^2 \text{ s.t. } |\theta_{i+1} - \theta_i| \leq \Delta\theta_{max} \quad (2)$$

for $i = 1, \ldots, N-1$ where "s.t." denotes "subject to", | . . . | denotes absolute value, N denotes the total number of CPs, $A_i$ is the area of the target-only region 62 for control point i (corresponding to $A_{CP_i}$ of Equation (1)), $A'_i(\theta_i)$ is the maximum portion of the area $A_i$ that is exposed for collimator angle $\theta_i$ with the leaves of the MLC 58 set to completely block radiation exposure of all OARs (corresponding to $A'_{CP_i}(\theta)$ of Equation (1)) and $\Delta\theta_{max}$ is the maximum change in collimator angle from one CP to the next along the arc. The optimization of Equation (2) entails optimizing the collimator angles $\theta_i$ for all control points $CP_1, \ldots, CP_N$.

The constraint on the optimization of Equation (2) assumes a constant gantry rotation speed over the arc so that $\Delta\theta_{max}$ is independent of the particular control point $CP_i$, but if the gantry rotation speed varies over the arc this can be accommodated by replacing $\Delta\theta_{max}$ with a control point-specific maximum collimator angle change $\Delta\theta_{i,max}$ (which will, in general, be smaller in portions of the arc where the gantry rotation speed is higher and larger in portions of the arc where the gantry rotation speed is lower). A constant collimator rotation speed is also assumed, but again this may differ in different parts of the arc. A higher collimator rotation speed permits larger changes in collimator angle from one control point to the next.

After completion of the geometric optimization 40, the main optimization 42 is performed with the collimator angle parameters set to the values $\theta_i$, i=1, . . . , N determined by the constrained minimization of Equation (2). The main optimization 42 then optimizes the MLC leaves and other parameters of the continuous arc radiation therapy plan. In some embodiments, the values $\theta_i$, i=1, . . . , N determined by the constrained minimization of Equation (2) are held constant in the subsequent main optimization 42. In other embodiments, the values $\theta_i$, i=1, . . . , N determined by the constrained minimization of Equation (2) are used as initial values which are further adjusted by the main optimization 42. It is noted that the positions of the leaves of the MLC used to define the target-only region portion areas $A'_i(\theta_i)$ in the optimization of Equation (2) are not transferred to the main optimization 42.

A rationale for the optimization of Equation (2) using the target-only region concept disclosed herein is as follows. The objective of radiation therapy optimization is to reach a balance between two competing goals: (i) delivering sufficient radiation dose to the PTV while (ii) sparing the surrounding OARs as far as possible. These two objectives are competing whenever the PTV and an OAR overlap in the BEV. Hence, increasing the geometric degrees of freedom for delivering the treatment will be helpful in radiation therapy. In line with this assertion, by choosing collimator angles $\theta_i$ that maximize the area of "target-only" portion in the BEV, the "geometric degree of freedom" of a beam is enhanced to an extent, which in turn increases the potential for arriving at a better solution for the optimization problem in VMAT. For instance, the collimator angle shown in FIG. 5 is geometrically advantageous as compared to the collimator angle shown in FIG. 4 for the given geometry of target volume and OARs.

In some embodiments, the geometric optimization 40 may also optimize other parameters. As already mentioned, the gantry rotation speed and/or collimator rotation speed may also be optimized. The number of CPs could also be optimized, e.g. specified by a gantry angle spacing or equivalently by the total number of CPs N.

In the optimization employing the target-only region 62, it is contemplated to consider fewer than all OARs defined by the dose objectives. For example, if one OAR is much more sensitive to radiation exposure than the others then the geometric optimization 40 may be performed with consideration to that single OAR while ignoring all other OARs. In a related variant, the various OARs may be assigned different weights of importance. One way to implement this is to use the weight to set a fraction of the total number N of CPs for which the OAR is considered. For instance, if OAR 1 is given a weight of 50 and OAR 2 is given a weight of 90, then OAR 1 will be considered in geometric optimization for only 50 percent of the total CPs, whereas OAR 2 will be considered in the geometric optimization for 90 percent of the total CPs.

In another variant, the target-only region 62 is computed by excluding only those portions of the PTV that overlap OARs located between the radiation source and the PTV, but not excluding those portions of the PTV that lie between radiation source and a "distal" OAR. This approach recognizes that the distal OAR receives less radiation exposure since radiation is absorbed in the intervening PTV. Note that in this case the position of an OAR (whether between the radiation source and the PTV or positioned with the PTV between the radiation source and the OAR) may depend on the location of the CP along the arc along which the radiation source traverses. Thus, for some control points a given OAR may be located between the radiation source and the PTV (and hence accounted for in determining the target-only volume) while for other control points that same OAR may be in the distal position (and hence ignored in determining the target-only volume).

It will be further appreciated that the disclosed continuous arc radiation therapy planning and subsequent therapy delivery may be embodied as a non-transitory storage medium storing instructions readable and executable by a computer to perform the disclosed operations (or to control the radiation therapy delivery device 50 to perform disclosed operations). For example, the non-transitory storage medium may be hard disk or other magnetic storage medium, and optical disk or other optical storage medium, a solid-state drive (SSD) or other electronic storage medium, various combinations thereof, or so forth.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A non-transitory storage medium that stores instructions readable and executable by a computer to perform a continuous arc radiation therapy planning method for planning a radiation therapy session parameterized by a set of parameters for control points (CPS) along at least one radiation source arc, the planning method comprising:

performing a geometric optimization on a sub-set of parameters of the set of parameters to generate optimized values for the sub-set parameters, wherein the geometric optimization does not include calculating radiation absorption profiles;

after completion of the geometric optimization, performing a main optimization on the set of parameters to generate optimized values for the set of parameters, wherein the main optimization is performed with the set of parameters initialized to the optimized values for the sub-set of parameters generated by the geometric optimization and comprises calculating radiation absorption profiles; and storing a radiation therapy plan comprising the optimized values for the set of parameters generated by the main optimization.

2. The non-transitory storage medium of claim 1, wherein performing the main optimization includes:

performing the main optimization with the optimized values for the sub-set of parameters held constant, whereby the optimized set of parameters generated by the main optimization includes the optimized values for the sub-set of parameters generated by the geometric optimization.

3. The non-transitory storage medium of claim 1, wherein the main optimization includes adjusting the optimized values for the sub-set of parameters, whereby the optimized set of parameters output by the main optimization comprises the adjusted optimized values for the sub-set of parameters.

4. The non-transitory storage medium of claim 1, wherein the sub-set of parameters includes collimator angle parameters specifying collimator angle of a multileaf collimator (MLC) at each CP of the CPs along the at least one radiation source arc.

5. The non-transitory storage medium of claim 4, wherein the sub-set of further comprises one or more gantry rotation speed parameters specifying rotation speed of a radiation source gantry and one or more collimator rotation speed parameters specifying rotation speed of the MLC at each CP of the CPs along the at least one radiation source arc.

6. The non-transitory storage medium of claim 4, wherein the geometric optimization is a constrained optimization that is constrained by a maximum collimator angle change between successive CPs of the CPs along the at least one radiation source arc.

7. The non-transitory storage medium of claim 1, wherein the geometric optimization comprises optimization of a cost function comprising a sum over the CPs along the at least one radiation source arc of a two-dimensional (2D) per-CP cost function wherein the per-CP cost function depends on one or more 2D regions in a beam's eye view (BEV) of the CP.

8. The non-transitory storage medium of claim 7, wherein the one or more 2D regions in the BEV of the CP consists of a target-only region defined as a planning target volume (PTV) excluding any portion of the PTV overlapping an organ at risk (OAR) region, wherein the PTV has a radiation dose objective and each OAR region has a maximum permissible radiation dose objective or constraint.

9. The non-transitory storage medium of claim 1, wherein the non-transitory storage medium further stores instructions readable and executable by the computer to operate a radiation therapy delivery apparatus in accord with the stored radiation therapy plan to deliver continuous arc radiation therapy to a patient.

10. A radiation therapy planning device comprising:

a computer programmed to perform a continuous arc radiation therapy planning method for planning a radiation therapy session parameterized by a set of parameters for control points (CPs) along at least one radiation source arc, the planning method comprising: (i) performing a geometric optimization on a sub-set of parameters of the set of parameters to generate optimized values for the sub-set of parameters, the sub-set of parameters comprising at least collimator angle parameters specifying collimator angles of a multileaf collimator (MLC) at the CPs along the at least one radiation source arc; and (ii) after completion of the geometric optimization, performing a main optimization on the set of parameters to generate optimized values for the set of parameters, wherein the main optimization is performed with the sub-set of parameters initialized to the optimized values for the sub-set of parameters generated by the geometric optimization; and a non-transitory storage medium operatively connected with the computer to store a radiation therapy plan comprising the optimized values for the set of parameters generated by the main optimization.

11. The radiation therapy planning device of claim 10, wherein the main optimization is performed with the optimized values for the collimator angle parameters held constant, whereby the optimized set of parameters output by the main optimization includes the optimized values for the collimator angle parameters.

12. The radiation therapy planning device of claim 10, wherein the main optimization includes adjusting the optimized the values of the collimator angle parameters.

13. The radiation therapy planning device of claim 10, wherein the sub-set of parameters further includes one or more gantry rotation speed parameters specifying rotation speed of a radiation source gantry along the at least one radiation source arc.

14. The radiation therapy planning device of claim 10, wherein the geometric optimization is a constrained optimization that is constrained by a maximum collimator angle change between successive CPs of the CPs along the at least one radiation source arc.

15. The radiation therapy planning device of claim 10, wherein: the geometric optimization comprises optimization of a cost function comprising a sum over the CPs along the at least one radiation source arc of a two-dimensional (2D) per-CP cost function; and the per-CP cost function depends on one or more 2D regions in a beam's eye view (BEV) of the CP.

16. The radiation therapy planning device of claim 15, wherein the one or more 2D regions in the BEV of the CP consists of a target-only region defined as a planning target volume (PTV) excluding any portion of the PTV overlapping an organ at risk (OAR) region.

17. The radiation therapy planning device of claim 10, wherein the geometric optimization does not compute radiation absorption profiles and the main optimization determines radiation absorption profiles.

18. A radiation delivery system including:

the radiation therapy planning device of claim 10; and a radiation therapy delivery apparatus comprising a radiation source mounted on a radiation source gantry, the radiation therapy delivery apparatus programmed to operate the radiation source gantry to move the radiation source along the at least one radiation source arc while delivering continuous arc radiation therapy to a patient in accordance with the radiation therapy plan stored in the non-transitory storage medium.

19. A computer implemented method including planning a continuous arc radiation therapy session parameterized by a set of parameters for control points (CPS) along at least one radiation source arc, the method comprising:

performing an initial optimization including adjusting values for a sub-set of parameters of the set of parameters to optimize a cost function comprising a sum over the CPS along the at least one radiation source arc of a two-dimensional (2D) per-CP cost function wherein the per-CP cost function depends on one or more 2D regions in a beam's eye view (REV) of the CP;

after completing the initial optimization, performing a main optimization on the set of parameters to generate optimized values for the set of parameters, wherein the main optimization is performed with the sub-set of parameters initialized to the optimized values for the sub-set of parameters generated by the initial optimization; and generating a radiation therapy plan comprising the optimized values for the set of parameters generated by the main optimization.

20. The computer-implemented method of claim 19, wherein the one or more 2D regions in the BEV of each CP of the CPs along the at least one radiation source arc comprises a target-only region defined as a planning target volume (PTV) excluding any portion of the PTV overlapping an organ at risk (OAR) region.

21. The computer-implemented method of claim 19, wherein the sub-set of parameters includes collimator angle parameters specifying collimator angle of a multileaf collimator (MLC) at each CP of the CPs along the at least one radiation source arc.

22. The computer-implemented method of claim 21, wherein the initial optimization is constrained by a maximum collimator angle change between successive CPs of the CPs along the at least one radiation source arc.

23. The computer-implemented method of claim 19, further comprising:

operating a radiation source gantry of a radiation therapy delivery apparatus to move a radiation source of the radiation therapy delivery apparatus along the at least one radiation source arc while delivering continuous arc radiation therapy to a patient in accordance with the generated radiation therapy plan.

* * * * *